United States Patent [19]

Koch

[11] Patent Number: 5,223,123

[45] Date of Patent: Jun. 29, 1993

[54] METHOD FOR MAKING A POLAROGRAPHIC OXYGEN SENSOR

[76] Inventor: Cameron J. Koch, 3503 117th Street, Edmonton, Alberta, Canada, T6J 1S2

[21] Appl. No.: 696,199

[22] Filed: May 6, 1991

Related U.S. Application Data

[60] Division of Ser. No. 403,832, Sep. 5, 1989, Pat. No. 5,030,336, which is a continuation of Ser. No. 66,979, Jun. 29, 1987, abandoned.

[51] Int. Cl.⁵ ............................................ G01N 27/404
[52] U.S. Cl. ........................................ 204/415; 65/59.1; 65/59.6; 204/153.17
[58] Field of Search ................. 204/153.17, 415, 420; 65/59.1, 59.6

[56] References Cited

U.S. PATENT DOCUMENTS

| | | | |
|---|---|---|---|
| 3,098,813 | 7/1963 | Beebe et al. | 204/415 |
| 3,334,623 | 8/1967 | Hillier et al. | 204/415 |
| 3,445,369 | 5/1969 | Porter et al. | 204/415 |
| 3,526,577 | 9/1970 | Molloy | 204/415 |
| 3,700,579 | 10/1972 | Clifton et al. | 204/415 |
| 3,855,095 | 12/1974 | Leonard et al. | 204/420 |
| 4,220,814 | 9/1980 | Kyle et al. | 65/59.6 |
| 4,269,685 | 5/1981 | Parker | 204/415 |
| 4,325,797 | 4/1982 | Hale et al. | 204/415 |
| 4,732,662 | 3/1988 | Holscher | 204/415 |

FOREIGN PATENT DOCUMENTS

| | | | |
|---|---|---|---|
| 344234 | 11/1921 | Fed. Rep. of Germany | 65/59.6 |
| 066687 | 8/1987 | France | 65/59.6 |

*Primary Examiner*—T. Tung
*Attorney, Agent, or Firm*—Dennison, Meserole, Pollack & Scheiner

[57] ABSTRACT

The cathode sub-assembly of a polarographic sensor comprises an elongate housing with a longitudinal opening therethrough and with noble metal wires extending completely through the opening, the wires held symmetrically in the longitudinal opening by an extensive plug of glass which is solidified in situ in sealing contact with the wires and with the wall of the longitudinal opening. A suitable tubular anode is provided through which the cathode sub-assembly protrudes, and a flexible membrane of an inert material, which is permeable to gas and impermeable to water vapor and other than gaseous dissolved solutes, is secured in sealed relationship over the anode and the cathode, with a film of electrolyte bathing the anode and the cathode and contained by the membrane.

5 Claims, 3 Drawing Sheets

METHOD FOR MAKING A POLAROGRAPHIC OXYGEN SENSOR

This is a divisional of copending application Ser. No. 07/403,832, filed Sep. 5, 1989, now U.S. Pat. No. 5,030,336, which is a continuation of Ser. No. 07/066,979, filed Jun. 29, 1987, now abandoned.

FIELD OF THE INVENTION

The present invention relates to polarographic sensors and to improved methods of making such sensors. Although this invention is particularly useful for sensors to be used chiefly for the measurement of oxygen, it will be recognized by those skilled in the art that most of the underlying principles and discussions will pertain equally to other types of polarographic sensors as well, and accordingly the present invention is not limited to oxygen sensors.

BACKGROUND OF THE INVENTION

The measurement of partial pressures and concentrations of oxygen is of great importance in many areas of biology, medicine, (bio)chemistry, (bio)physics and engineering. This measurement can be accomplished with various degrees of accuracy and resolution using a wide variety of instrumentation and methodology, from simple manometric and chemical assays to high resolution gas chromatography, neutron activation and position emission tomography. Techniques used to measure oxygen content in solids (which will not be discussed) differ substantially from those used to measure oxygen content in liquids and gases, and for the last two phases, the techniques can vary substantially depending on the physical and chemical environment of the sample.

For temperatures in the biological range (e.g. 0°-50° C.) it is often necessary to measure and/or control oxygen concentrations both in the gas and the liquid phase and this type of measurement can only be made with a membrane covered polarographic sensor of the type disclosed in U.S. Pat. No. 2,913,386, issued Nov. 17, 1959 to Leland C. Clark, Jr., and hereinafter referred to as a "Clark" sensor. In this type of sensor, oxygen is reduced by a noble metal cathode, whose potential is fixed with respect to a reference anode (often Ag-AgCl), both elements of the cell in an aqueous electrolyte and enclosed by a gas-permeable membrane. Unfortunately, many scientific studies involve reactions which are modulated by very small concentrations of oxygen and both the resolution and the response time of typical Clark sensors are often inadequate in monitoring such reactions (C. J. Koch, Oxygen Effects in Radiobiology. In: Hyperthermia (Hl Bicher & DP Bruley, eds) Adv. Exp. Med. & Biol., Vol. 157, 123-144, Plenum Press, New York, 1983).

One can easily list several criteria of importance in determining the overall quality of a sensor. Some of the criteria are quantitative in that absolute numbers can be assigned to them:

1a) Sensitivity: the magnitude of the response produced by a given partial pressure of oxygen (e.g. 0.5 nanoamps [nA] per kilopascal [kPa] of oxygen partial pressure [$pO_2$]). The current generated by the sensor will be directly related to the amount of oxygen consumed by the sensor-see 8a below for importance-and below a certain value, the current becomes increasingly difficult to measure accurately (state-of-art circuitry allows the measurement of currents below 1 picoamp only with great difficulty and cost).

2a) Minimum Value of "Zero" Current: the equilibrium value of response as a function of some reference value for a sensor in an environment of zero oxygen (e.g. 0.1% of response in air).

3a) Stability of "Zero" Current: the change in response of a sensor in an environment of zero oxygen per unit time (can include linear, exponential and random components).

4a) Noise: the random fluctuations in response of a sensor in high or low concentrations of oxygen (e.g. % of air value or % of scale).

5a) Stability: the relative change in response (i.e. current) of a sensor per unit time in a constant environment ($pO_2$, ionic strength, temperature) (e.g.-0.5%/hr).

6a) Linearity: the range of oxygen radial pressures over which the relationship between oxygen partial pressure and sensor response is linear to some specified accuracy (it is common for sensors to deviate from linearity at very high and at very low partial pressure of oxygen).

7a) Response Time: the time for a given percentage change in response after a step change in oxygen partial pressure in the external environment of the sensor (usually 1/e of step value). An ideal sensor would approach the new value exponentially with a single time constant but most sensors have two or more associated time constants, the relative importance of which depends upon the absolute values of oxygen partial pressure before and after the step change. Usually the most stringent test involves a step change in oxygen partial pressure from a high value (i.e. ambient air) to zero.

8a: Stirring Requirements in Liquids: the required velocity of the liquid of interest to minimize the response differential of the sensor between gas and gas-equilibrated liquid. This parameter should be expressed both as liquid-sensor velocity to achieve a given percentage of the gas phase response, and as maximum percentage decrease when the sensor is added to an unstirred solution which was in equilibrium with the gas phase.

Other aspects of sensor design can be just as important for practical usage but are inherently qualitative in nature.

9a) Shielding Efficiency: the relative isolation of the performance of a sensor and its associated electronic amplifier in the environment of other laboratory equipment and larger moving charged bodies (people).

10a) Structure: the aspects of shape, size and materials of sensor construction which may enhance or limit its range of applications. For example, there would be no point in having a sensor which could measure oxygen accurately at low levels but which could not be sealed into a closed volume without leakage or presence of air bubbles etc. It is equally important that the sensor body have a stable shape (e.g. plastics swell in water that this shape be suitable for fitting into a variety of standard vessels (e.g. many commercial sensors have their active tip as the widest part of the sensor, making it impossible to insert into standard fittings without disconnecting the sensor or having to reapply the membrane). An often overlooked factor is the contamination of the bulk of the sensor by oxygen and other chemicals from previous environments and conversely the contamination of samples by materials from the bulk of the sensor. For example if one is attempting to monitor an oxygen dependent reaction in a small closed volume, the plastic body of a sensor can give off large quantities of dissolved oxygen.

11a) Consistency of Response to Changes in Environment: the consistency of sensor response to changes in sensor environment such as pressure (i.e. one would hope to obtain the same response with 1% oxygen plus 99% nitrogen at 101 kPa pressure, as with 100% oxygen at 1.01 kPa pressure). In addition, the temperature dependence of the sensor should be reproducible and without hysteresis. Often one is required to monitor oxygen concentrations in an extremely humid environment and this poses rather severe problems for the electrical connections to the sensor, because large leakage currents can result from damp connections and cable.

12a) Electronic Amplification Requirements (see also 5a): the current gain necessary to accurately convert the oxygen-derived sensor current to a form suitable for monitoring purposes—usually a full scale output of the order of 1 volt. Sensors available at the present time have a very broad range of sensitivities ($10^{-10}$–$10^{-7}$ A/kPa $pO_2$). One usually obtains the highest sensitivities at the expense of some other quality factors. Since many experiments require measurements of the order of 0.01 kPa of oxygen partial pressure, the resolution of the amplification system must be at least as sensitive as $10^{-12}$ A and preferably even better for the less sensitive devices. Thus, the development of significantly better sensors requires state-of-the-art electronic measurement techniques.

13a) Interference: the response of the sensor to any other than the desired molecule which can diffuse through the membrane and react with the redox-processes ongoing. Several gases have been reported to do so with polarographic oxygen sensors ($CO_2$, $N_2O$, $H_2S$, $SO_2$, $NO$, $NO_2$) but it may be possible to reduce such interference by proper mechanical and electrochemical design.

Commercial prior art polarographic oxygen sensors include those manufactured by Beckman Instruments (Model 325814-no longer available, and patented under aforesaid U.S. Pat. No. 2,913,386, issued Nov. 17, 1959 to Leland C. Clark, Jr.), Yellow Springs Instruments (Model 5331, disclosed in U.S. Pat. No. 3,406,100 issued Oct. 15, 1968 to Everett W. Malloy), and Diamond Electrotech (formerly Transidyne General Corporation-Model 730).

One can much more easily appreciate the concepts of response time, zero current and noise by measuring as a function of time the response of an oxygen sensor after its environment is rapidly changed from a high oxygen partial pressure (i.e. air) to zero. Such measurements, using the best responders of several each of the sensors described above, have shown an initial rapid decrease in current to 2-10% of that in air, but then a much slower decrease, taking many hours, to a minimum value of 0.2-2% of that in air. Some of the poorer responders had zero currents several fold higher and more in keeping with their actual specifications. Others had zero currents which remained large and variable.

Furthermore, it was found that the magnitude of the zero current was not independent of the previous environment of the sensor (C. J. Koch and J. Kruuv, Measurement of the very low oxygen tensions in unstirred liquids. Analyt. Chem. 44 1258-1263, 1972), and this probably points to one source of the zero current, namely dissolved oxygen in the body, typically plastic, of the sensor itself. Under some circumstances one can measure small quantities of oxygen in the presence of a large zero current if one is able to continually switch back and forth between the gas to be monitored and a true "zero oxygen" gas but this is seldom possible. Such switches for measurements in liquids are virtually impossible.

The highly variable nature of the zero current and the other response parameters led the present inventor to believe that flaws in available sensors were expressing themselves to varying degrees, and that perhaps a much improved sensor would be possible if these flaws could be identified and corrected. Unfortunately, the flaws have been "over" identified in the literature, since changing almost any aspect of the operation of a sensor changes its response to some degree. Therefore, the approach taken was to re-examine the basic aspects of the design and operation of the polarographic sensors, to see if flaws could be predicted in their performance and to devise construction methods to correct or minimize these flaws.

The electrochemical processes have not been described quantitatively but there is certainly general agreement about the basic anode and cathode reactions (see Irving Fatt: "Polarographic Oxygen Sensors", CRC Press, Cleveland 1976; D. J. G. Ives and G. H. Janz: "Reference Electrodes", Academic Press, New York, 1961).

$$\text{At Cathode: } O_2 + 4e^- + 4H^+ \rightarrow 2H_2O \quad (r1)$$

Note that $H^+$ and other cations present in the electrolyte will be attracted to the cathode so that the "pH" near the oxygen reductive surface will be more acidic than the "pH" of the electrolyte as mixed in bulk solution.

$$\text{At Anode: } 4Ag + 4Cl^- \rightarrow 4AgCl + 4e^- \quad [r2]$$

The converse will be true for the anode (i.e. $OH^-$ and anions attracted) but the surface area of the anode is usually so much larger than that of the cathode, that pH changes would only be expected to effect the cathode reactions.

Although reactions r1 and r2 are often given in descriptions of polarographic sensors, there is not much evidence that they actually occur in this manner. For example, it is clear that almost all non-enzyme mediated (and probably most enzyme-mediated) redox reactions occur in 1 electron steps. This means that the 4 electron reduction would have to proceed through $O_2^-\bullet$ or $HO_2\bullet$, $H_2O_2$ and $OH\bullet$.

$$O_2 + e^- + H^+ \rightarrow O_2^-\bullet + H^+ \eta pKa = 4.3 \rightarrow HO_2\bullet \quad (r3)$$

$$O_2^-\bullet + e^- + 2H^+ \rightarrow H_2O_2 \quad [r4a]$$

or $$2O_2^-\bullet + 2H^+ \rightarrow H_2O_2 + O_2 \quad [r4b]$$

or $$HO_2\bullet + e^- + H^+ \rightarrow H_2O_2 \quad [r4c]$$

or $$O_2^-\bullet + HO_2\bullet + H^+ \rightarrow O_2 + H_2O_2 \quad [r4d]$$

$$H_2O_2 + e^- \rightarrow OH^- + OH\bullet \quad [r4]$$

$$OH\bullet + e^- \rightarrow OH^- \quad [r6]$$

Reactions r4a and r4b are likely to be extremely slow. Even reaction r5 is much slower than reaction r3. In fact, at relatively low polarizing voltages (e.g. 0.55 volt) the response of a typical oxygen sensor (without its membrane) is a deoxygenated hydrogen peroxide solution is less than 1/10th that in a solution with the same concentration of oxygen (unpublished observation). From inspecting these reactions, and noting that the electrolyte tends to become more basic, one might expect that the optimal pH for sensor operation might fall within the acid range. This is because the very slow reactions (r4a and r4b) must predominate an neutral and higher pH's. However, in agreement with other investigators this inventor has found the most reproducible responses under basic conditions. Similarly, in agreement with Hahn et al. (C. E. W. Hahn, A. W. Davis & W. J. Albery, Electrochemical Improvement in the Performance of $pO_2$ Electrodes, Resp. Physiol. 24, 109–133, 1975) this inventor has sometimes found an improved and more stable zero current when a trace of catalase is added to the electrolyte. With the sensors according to the present invention, which already have a much reduced zero current, the presence of catalase can cause negative currents in the absence of oxygen. This may be due to a preferential build-up of superoxide which may actually be oxidized rather than reduced in the absence of oxygen. The point of this discussion though is that an "improved" response of a particular sensor under certain specified conditions may result from more than one interacting phenomena. Thus, the improvement may not be found under other circumstances and its cause may not be fully understood.

The linearity of a Clark senor depends on the condition that the reduction of oxygen and its reduced products (reactions r3 to r6) at the cathode maintains their concentration in the immediate vicinity of the cathode at essentially zero. Thus, since the oxygen gradient across the membrane will be linear (there is no oxygen consumption within the membrane), the flux of oxygen through the membrane will simply be proportional to the oxygen partial pressure in the environment external to the membrane (external environment). The proportionality constant must allow for the very different solubility and diffusion constants of the external environment, the membrane and the electrolyte. The flux of oxygen from the external environment can cause a decrease in partial pressure at the interface of membrane and external environment if the diffusion constant of the external environment is small enough and/or the flux is large enough. Thus in order to minimize the difference in sensor response between gas and gas-equilibrated liquid, it is desirable to decrease this flux by increasing the relative diffusion barrier of the membrane (i.e. thicker membrane or smaller diffusion constant) and/or decreasing the size of the cathode. There is a tradeoff involved however because these measures have the effect of reducing the sensitivity.

BRIEF DESCRIPTION OF THE DRAWINGS

The invention will be readily understood from the following description of prior art and of a preferred embodiment thereof given, by way of example, with reference to the accompanying drawings, in which.

Figure 1:
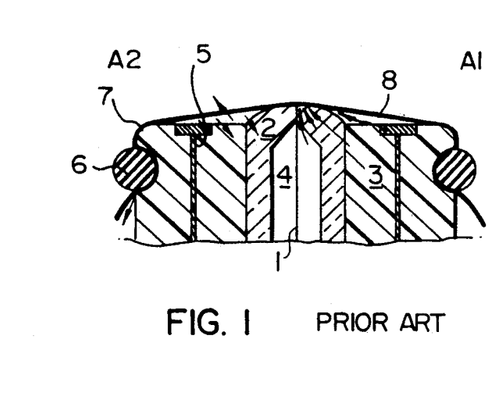
FIG. 1 shows a view in longitudinal cross-section through a polarographic sensor representative of prior art sensors.

In FIG. 1, there is illustrated a prior art polarographic sensor which is generally representative of the above-mentioned Beckman Model No. 325,814 and Yellow Springs Model No. 5331 sensors.

This representative sensor comprises a platinum wire cathode 1 provided within a body of resin material in the Yellow Springs sensor or within a glass enclosure 2, which projects from one end of a housing 3 of plastic material, the cathode extending through a space 4 filled with air, in the above Beckman sensor. An anode 5 is provided in the form of a silver wire (Beckman) block or film (Yellow Springs) and an O-ring 6 retains a membrane 7 covering the top of the sensor and enclosing a supply 8 of KCl.

Also, in FIG. 1 potential sources of oxygen leakage, which occurs primarily along the seal of the cathode 1 through the glass enclosure 2 and the space 4, through the housing 3 and along the sealing of the anode 5, are represented diagrammatically by arrows A1 at the right-hand side of FIG. 1 and sources of electrolyte loss, which occurs primarily at the O-ring seal, the membrane 7 and into the housing 3, as indicated above, are represented diagrammatically by arrows A2 at the left-hand side of FIG. 1. The Yellow Springs sensor has its greatest diameter at the O-ring, so insertion into leak-proof fittings is impossible after membrane assembly. The overall tip diameter if too wide to allow sufficient stretching of relatively thick and non-elastic Teflon membranes which can minimize electrolyte loss. Both sensors require machining of their plastic bodies to ensure a leak-proof seal with, for example, Ultra-Torr ® fittings (manufactured by Cajon) because of imperfections in the plastic casting.

A fundamental design decision of an embodiment of the present invention described in greater detail below was to device methods which would isolate as completely as possible the cathode, the anode and their associated reactions/reaction products (reaction elements) from the influence of both internal (i.e. from within the sensor) and external contaminants or chemical and/or physical modulations.

Possibly the most important problem of sensor construction is the mechanical seal of the cathode within the sensor body itself. One can appreciate the magnitude of this problem by calculating the leakage involved with a typical engineering specification for a "hermetic" seal (e.g. $5 \times 10^{-9}$ cc per second atmosphere (101 kPa) of differential pressure). If this amount of oxygen were leaking to the cathode from some source within or outside the sensor then the current from this "leakage" would be: $5 \times 10^{-9}$ (cc per sec per 101 kPa)$\times 1$ (mole per 22400 cc)$\times 6 \times 10^{23}$ (molecules per mole)$\times 4$ (electrons per reduced oxygen molecule)$\times 1$ (coulomb per $6 \times 10^{18}$ electrons)$= 10^{-7}$ amps per 101 kPa.

That is, if the external oxygen partial pressure to be measured were zero, but oxygen could leak to the cathode at the above rate, a "zero" current of 100 nanoamps would still flow. This is many times greater than the aerobic sensitivity of typical sensors with small (<0.1 mm) diameter cathodes. To have a meaningful "zero" current, the leakage rate of oxygen to the cathode form all sources should be perhaps 100,000 times less than the engineering standard of a leak-proof seal. Although some polarographic sensors with very large cathodes (e.g. Yellow Springs Model 5331) seal their cathode directly into a plastic, this technique will not work well with small cathodes because oxygen diffusion out of the plastic will lead to the above problems.

A somewhat less stringent seal of the anode may be necessary since oxygen which leaked past this seal would have to diffuse along the thin film of electrolyte and would have the opportunity to diffuse out of the membrane. However, it should be noted that oxygen leakage past the anode could be important if the sensor were monitoring the oxygen partial pressure in a small volume, since this would cause the equivalent of an overall leakage into the monitored volume. Other requirements for the anode have not been studied carefully. Silver/silver chloride is often used since silver chloride is insoluble in water and hence its activity does not change with continued sensor use. This stability, while generally acknowledged (Irving Fatt: "Polarographic Oxygen Sensors", CRC Press, Cleveland 1976) has been disputed by Clark (L. C. Clark, Electrolytic sensor with anodic depolarization. U.S. Pat. No. 3,380,905, issued Apr. 30, 1968 to L. C. Clark, Jr.,) A general feature that is often mentioned is that the anode should have an area of at least 50 times that of the cathode. However, it may be that much larger anodes are desirable and many of the leakage characteristics previously identified for the cathode may also apply to the anode. One problem that exits with available sensors is that the anode and its connecting wire, usually a linear or spiral wire adjacent to or around the cathode, do not provide a continuous electrical shield of the cathode. This problem has been addressed in sensors with an all-metal body, but this metal represents a major contamination problem since even stainless steels are attacked by many of the commonly used salts. Furthermore, the metal body can cause ground loop or other electrical isolation problems since most apparatus is already grounded.

Since the active tip of the senor has a voltage imposed between conducting elements (the anode and cathode) the resistivity of the sensor body should be as high as possible. Although the bulk resistivity of many otherwise suitable materials (e.g. epoxides) can be very high, the surface resistivity is often not specified and can be greatly influenced by the aqueous electrolyte. It is pointed out that in order to measure currents in the picoamp range, and with an anode-cathode voltage of greater than 0.5 volts, the resistivity of all components of the connectors, cable and sensor would have to be greater than 500,000 megohms. This value, while realizable under some conditions in practice, is certainly beyond the specifications of all components presently available except perhaps for Teflon and some electrical sealing glasses. Bulk resistivities of epoxides and other plastics vary by many orders of magnitude but typically are in the range of $10^{10}-10^{17}$ ohm cm. However, most components and materials are specified for operation at high voltage ($>>1$ volt) where all kinds of conduction are possible. For polarographic sensors operating at voltages of roughly 0.5, only conduction-band conduction and electrochemical redox processes are possible and of course the dominant redox process is the desired reduction of oxygen. Therefore, some desirable features of the design of a high quality sensor are:

1b) a near perfect seal of the anode and cathode is preferable:

2b) extremely high resistivity materials are preferable throughout, especially at the active tip of the sensor which is covered by electrolyte; and 3b) a method should preferably be provided for adequate shielding of the high-impedance cathode.

The requirements of the electrolyte film are contradictory. On the one hand, the electrolyte must pass the sensor current via ionic flow without any appreciable drop in potential. If this were not the case then the anode/cathode potential would change with current, leading to non-linearities in current vs. oxygen partial pressure. This implies that a relatively thick film of electrolyte (and/or high dissolved salt concentration) with low resistivity would be required. On the other hand, the cathode must be able to reduce all of the oxygen in its vicinity as rapidly as possible, to allow a fast response time to changing oxygen partial pressures, and this suggests the need for as thin a film as possible. It is likely that a thin film would also be required to confine the products of the reduction reactions (r3 to r6) so that reduction and/or dismutation will always be near completion. Thus 4b) Some of the one-electron reductions may need to be catalyzed and may even be partially reversible or reactions r4 to r6 may be chemical dismutations rather than electrochemical reductions.

5b) The cathode should preferably be small to allow the theoretical operating condition of zero oxygen partial pressure at the cathode surface, but of a sufficient size to allow reasonable sensitivity; and 6b) The shape of the anode and electrolyte film should preferably be made to allow condition (5b), yet minimize the cathode-anode resistance.

Another aspect of the sensor's construction which is desirable for maintaining the electrolyte composition (and hence the sensor response) constant is the method of containment of the membrane and electrolyte. This subject has been the subject of several papers and patents (see U.S. Pat. Nos. 3,887,194; 3,575,836; 3,445,369; 3,577,332; 4,325,797 and Irving Fatt: "Polarographic Oxygen Sensors" CRC Press, Cleveland 1976).

The electrolyte volume should be large enough to prevent significant changes in composition (i.e. pH and $Cl^{-1}$) during the lifetime of operation between membrane changes. The gas-permeable membrane should preferably be impermeable to water vapor to prevent dessication of the electrolyte, particularly when operating at low hydrostatic pressure or in dry gases. A membrane which has suitable properties of electrolyte retention and gas permeability may become mechanically flawed during application, which typically involves stretching a planar material over a rod-shaped sensor. Improved methods to do so while radially support (C. J. Koch and J. Kruuv, Measurement of Very Low Oxygen Tensions in Unstirred Liquids. Analyt. Chem 44 1258–1263, 1972) and tensioning (J. A. Porter and A. F. Dageforde, Membrane Tensioning Means and the Use Thereof. U.S. Pat. No. 3,887,194, issued Jun. 3, 1975 to Porter et al.) the membrane have been described. The present invention also includes a simple pre-stretching procedure which is important for relatively non-elastic membranes.

Electrolyte can also be lost due to an incomplete seal of the membrane against the body of the sensor. Okun et al. suggested many years ago that a plastic, cylindrical membrane retainer would be superior to the O-ring which is typically used by most manufactured sensors (U.S. Pat. No. 3,227,643, issued Jan. 4, 1966 to D. A. Okun et al.). A recent patent by Hale (J. M. Hale, Membrane Mounting Method and Membrane-Enclosed Amperometric Cell. U.S. Pat. No. 4,325,797, issued Apr. 20, 1982 to Hale et al.) suggests the use of a precision, non-elastic double-tapered membrane retainer but this devices is stated not to be useful for relatively non plastically deformable membranes such as Teflon.

Similarly electrolyte can be lost through water absorption by the body of the sensor itself (many plastics will absorb a substantial percentage of water). Water can also be lost via a slow diffusion along the surface roughness of the sealing area and conversely other molecules may be able to enter the electrolyte.

If the sensor's response is to depend only one the oxygen partial pressure, and not the hydrostatic gas pressure, then the membrane should be stretched and held in place tightly enough to resist deformation at low or high external pressures, particularly if the external pressure drops below the vapor pressure of the electrolyte. Sensor instabilities caused by changes in pressure increase if small gas bubbles develop in the volume normally filled by electrolyte.

A final technical problem involving the actual use of commercial oxygen sensors is that after membrane application, the sheet of membrane is trimmed around the membrane retainer (typically an O-ring). This trimming process leaves a "ruffled skirt" of residual membrane which traps air bubbles and makes the sensor tip difficult to clean. The trapped air bubbles limit accuracy when using small samples or low oxygen concentrations since a given volume of oxygen-containing gas contains about 40 times more oxygen molecules than a similar volume of gas-equilibrated water. In some cases, plastic caps attached (usually via a screw thread) over the sensor tip have been used to cover the residual membrane U.S. Pat. No. 3,445,369, issued May 20, 1970 to J. A. Porter et al.), but these caps inevitably contain trapped gas and/or liquids and increase the total amount of plastic material exposed to the solution to be measured. A similar trapping would be found for the precision non-elastic retainer described above (U.S. Pat. No. 4,325,797, issued Apr. 20, 1982 to Hale et al.). In summary, the containment of the electrolyte should preferably allow for:

7b) a water and ion tight seal to allow operation at reduced pressures, in dry gases or in solutions of significantly different composition than the electrolyte (e.g. pH, osmolality, ion content, presence of solvents);

8b) counteracting absorption of the electrolyte by the sensor body;

9b) sufficient volume to maintain the electrolyte concentrations (pH, $Cl^-$) constant;

10b) sufficiently strong membrane and seal to resist plastic deformation due to pressure changes in the external environment and a method to eliminate any residual membrane distal from its retainer which could prevent easy cleaning and which could trap gas bubbles; and 11b) minimization of air or liquid traps, or materials which could cause cross-contamination between sequential measurements.

Brief Summary of the Embodiment

It is a principal object of the present invention to provide a polarographic sensor having an improved isolation of the polarographic reactions ongoing in said sensor either from modulating influences caused from sources internal to said sensor or from sources in the external environment of said sensor and an improved isolation of the possibly modulating effect of said sensor on said external environment.

According to the present invention there is provided, in a polarographic sensor, a cathode sub-assembly made from an elongate housing with a longitudinal opening therethrough and with nobel metal wires extending completely through said opening, said wires held symmetrically in said longitudinal opening by an extensive plug of glass which is solidified in situ in sealing contact with said wires and with the wall of said longitudinal opening. Preferably, the elongate housing, the cathode and the sealing glass have at least similar coefficients of thermal expansion. A suitable tubular anode is provided through which said cathode sub-assembly protrudes, and a flexible membrane of an inert material, which is permeable to gas and impermeable to water vapour and other than gaseous dissolved solutes, is secured in sealed relationship over said anode and said cathode, with a film of electrolyte bathing said anode and said cathode and contained by said membrane.

Advantageously, the cathode sub-assembly is enclosed by a second elongate housing portion which incorporates the above-mentioned anode, hereinafter referred to as the combined anode/body sub-assembly. This second housing is also made of inert, electrically non-conductive material and with an elongate opening therethrough.

A suitable material for both elongate housings has been found to be a ceramic manufactured by Corning under the Trade Mark Macor ® which, further, offers the advantage of enabling precision machining of the elongate housings to be effected.

In a preferred embodiment, the longitudinal opening of the end of the anode/body sub-assembly which will become the active or measuring tip of the completed sensor, is convergently tapered to a frusto-conical shape receiving in sealed engagement therewith a complementary, precision-machined outer convergently tapered surface on the active end of the cathode sub-assembly said sealed engagement being mediated by an epoxy adhesive.

The exterior surface of the active end of the body housing has a precision-machined convergently tapered frusto-conical shape fitted into sealed engagement with a precision-machined internal surface on the anode.

In a preferred embodiment of the invention, an electrically conductive coating is provided internal to the anode/body sub-assembly for providing a connection to the anode, the conductive coating extending around both ends of the body housing and shielding the cathode. This coating advantageously compromises a fired, thick film composite of precious metal and glass.

Furthermore, in a preferred embodiment of the invention, the sensor has, at the active end thereof, a tip portion having a cylindrical outer surface and peripheral serrations formed in the cylindrical outer surface, and wherein the sensor further compromises cylindrical retaining means fitted over the cylindrical outer surface in co-axial relationship therewith and retaining the membrane in clamped relationship around the cylindrical outer surface between the cylindrical retaining means and the cylindrical outer surface. The membrane has a periphery which is entirely contained between the cylindrical outer surface and the cylindrical retaining means to counteract the retention of trapped gases at the membrane periphery.

DESCRIPTION OF THE PREFERRED EMBODIMENT

Figure 2:
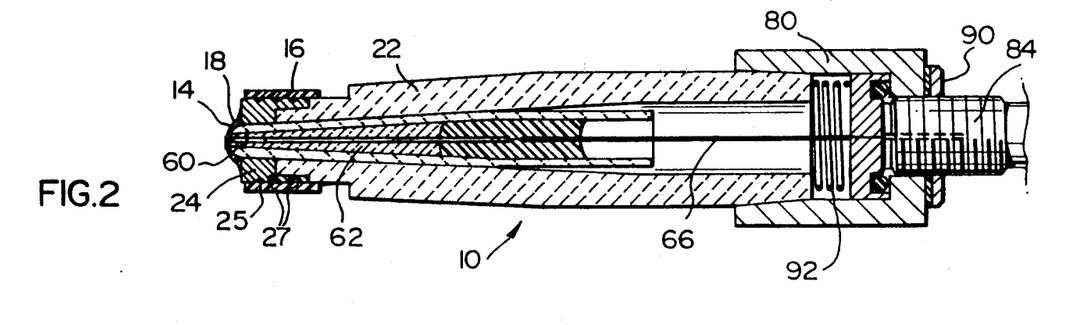
FIG. 2 shows a view taken in longitudinal cross-section through a polarographic sensor embodying the present invention.

Referring now to the polarographic oxygen sensor illustrated in FIG. 2 of the accompanying drawings, which shows a preferred embodiment of the present invention, it is first pointed out that the design of this sensor was effected taking into account the following eight principal objectives:

(1) minimization of plastics throughout;

(2) an improved seal of the cathode electrode which at the same time allowed versatility with respect to number of cathode elements, materials, size and shape;

(3) a pure silver anode of very great area compared with that of the cathode, which totally surrounded and shielded the cathode, and which would not allow leakage of oxygen from internal or external sources;

(4) a body which allowed a complete electrostatic shield of the cathode;

(5) a body with excellent structural stability and which was biological and chemically inert;

(6) a body which could be precisely machined to fit standard-taper leak-proof fittings;

(7) a leak-proof membrane retention system resistant to changes caused by variations in external environment and with no residual membrane (which can trap air bubbles and increase the difficulty of cleaning); and (8) a modular design which allowed flexibility of construction, testing of key components and straightforward assembly.

It may be appreciated that although some of the above principles have been previously identified, their actual implementation has often been compromised. Even with these compromises, many patented devices have never been produced commercially. This undoubtedly stems from the extraordinarily complex machining and assembly requirements of typical, previous sensors and a further objective of the present design was to reduce this complexity without compromising the other objectives.

Figure 5:
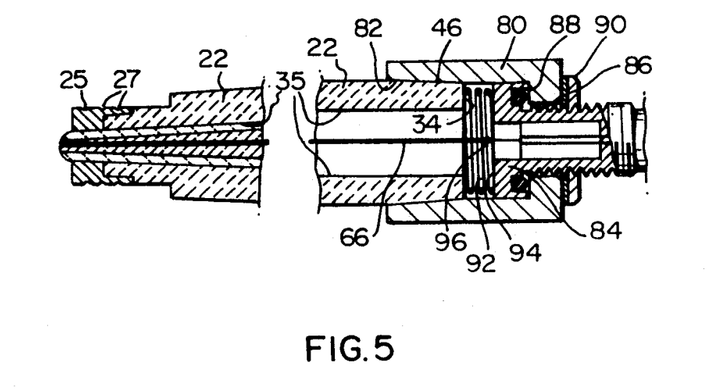
FIG. 5 shows a broken-away view of front and back ends of the components of FIG. 3, with the addition of a completed anode and the active end of the cathode sub-assembly of FIG. 4 at the front, and with a connector assembly at the back.
Figure 6:
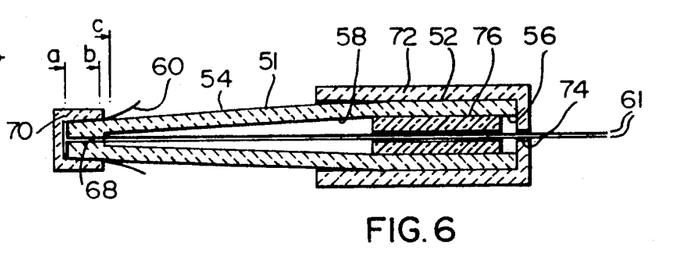
FIG. 6 shows a view in longitudinal cross-section through components of a cathode sub-assembly of the sensor of FIG. 2 during manufacture of the subassembly, and related clamping devices.
Figure 6A:
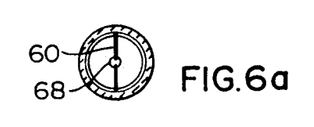
FIGS. 6a, 6b and 6c show views taking in cross-section along the lines a, b and c respectively of FIG. 6.
Figure 6B:
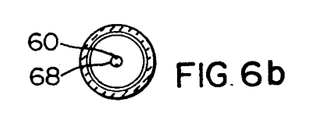
Figure 6C:
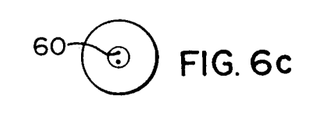

The preferred embodiment of the sensor, as described below, comprises several component parts or sub-assemblies, namely an anode/body sub-assembly, shown as its component parts in FIG. 3, a cathode sub-assembly, shown in FIG. 4, a connector sub-assembly shown as part of FIG. 5, and a membrane retainer and membrane, shown in FIG. 7. Additionally, FIG. 6 provides a detailed view of the steps involved in the sealing of the cathode wires into the cathode sub-assembly.

In the following description, the orientation of the elements of the sensor are described with reference to an active tip or front end of the sensor at the left, and to the connector or back end of the sensor at the right, as shown in the drawings.

Figure 3:
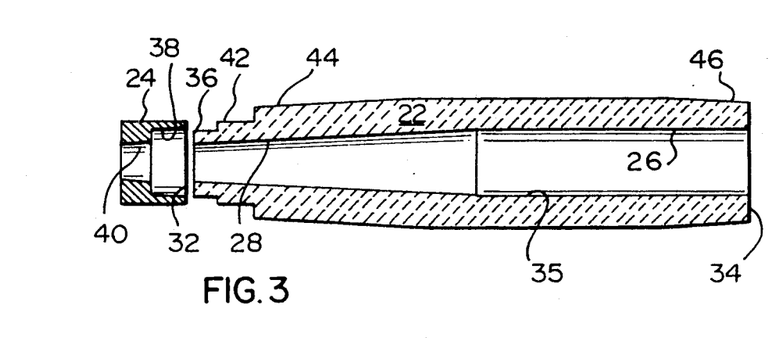
FIG. 3 shows a view in longitudinal cross-section through components of the senor of FIG. 2.

Referring now in greater detail to FIGS. 2 and 3, the sensor is indicated generally by reference numeral 10 and comprises an elongate ceramic housing 22, coated on its interior surface and opposite end surfaces 32, 34 with an electrically conductive film 35 and with a solid silver anode 24 mounted at the front end, the housing 22 having an axial opening or passage extending therethrough. The passage extends (from the center) backwardly with a cylindrical surface 26 and forwardly with a left convergently tapered or frusto-conical surface 28 extending to the front end of the sub-assembly. The electrical conductive film 35 comprises a thick film composite made form precious metal and glass (e.g. Thick Film Systems Multifire ® 3580), which is fired in sealing contact with surfaces 26, 28, 32 and 34 by placing the coated housing 22 in a furnace at a temperature of 750° C. for a period of thirty minutes. At its external front end the ceramic housing 22 is previously machined to provide a forwardly convergent, tapered frusto-conical outer surface 36.

An anode 24 is made from a rod of solid pure silver, with an internal frusto-conical surface 38 being machined into the back end of the rod and being dimensioned so as to be exactly complementary to the frusto-conically tapered outer surface 36 of the ceramic housing 22. Also, a forwardly convergent frusto-conical opening 40 is machined through the anode, this taper forming a continuation of the forward passage 28 on the interior of the housing 22.

After being carefully cleaned, the anode is etched in hot, 0.1N nitric acid and is then secured to the housing 22, by high quality epoxy, the components being held together under pressure during cure of the epoxy material to form an anode/body sub-assembly. This pressure results in a stable mechanical fixture of these components, and in addition ensures good electrical contact between the anode 24 and the metal film 35 on the end face 32 of the housing 22.

After attaching the anode to the body, the anode is machined to the same diameter as the cylindrical shoulder 42 of the housing and peripheral serrations 25, 27 (see FIG. 5) are added to the anode to improve the seal of the membrane by its retaining sleeve (described below).

The housing 22 has two other externally machined surfaces which will be described in more detail below; near the front end, a forwardly tapered frusto-conical surface 44, and at the back end a backwardly tapered frusto-conical surface 46.

Figure 4:
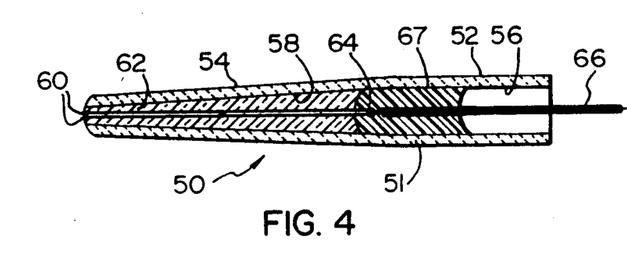
FIG. 4 shows a view in longitudinal cross-section of a complete cathode sub-assembly.

The cathode sub-assembly, indicated generally by reference number 50 in FIG. 4, is made from a smaller elongate ceramic housing 51 whose exterior surface has a cylindrical back end portion 52 and an externally frusto-conically tapered front end portion 54. An axial opening or passage therethrough follows the contour of the external shape with a back cylindrical internal portion 56 and a forwardly convergent tapered front internal portion 58. A pair of cathode wires 60 extend through the passage from the front end of the housing and are connected by solder 64 to a Teflon-covered multistrand wire 66.

In the front end of the passage 58 the cathode wires 60 are embedded in a glass seal 62, which fills the space between the cathode wires 60 and the surface of the passage 58.

At the back end of the housing 51, the cathode wires 60, the solder 64 and a length of the multistrand wire 66 are embedded in an epoxy material 67.

The external tapered front end surface 54 of the housing 51 of the cathode sub-assembly 50 has a shape which is exactly complementary to the front portion 28 of the conductive-film-covered interior passage in the housing 22 and the opening 40 in the anode. The cathode sub-assembly is fixed into this passage using an epoxy adhesive (see FIG. 5).

The back or right hand end of the housing 22 is formed with a backwardly convergent, tapered or frusto-conical outer surface 46, which is fitted in tight engagement (see FIG. 5) with a complimentary internal surface 82 formed in an end cap 80, which serves to retain a SMA or Sub-Minax coaxial receptacle 84 (of e.g. Amphenol 901-190 or 27-12) relative to the housing 22.

The coaxial receptacle 84 is slidingly received in a cylindrical axial opening 86 in the end cap 80, which is provided at its back end with an inwardly directed annular flange 88 for retaining the receptacle 84 which is fastened to the end cap by a lockwasher and nut 90. A nickel-plated helical compression spring 92 is provided between the plated back surface 34 of the housing 22 and the front surface 94 of the coaxial receptacle 84 and serves to make an electrical connection between the receptacle's outer surface (ground) and the conductive film 35 which in turn makes an electrical connection with the anode 24. The central terminal 96 of the receptacle 84 is connected to the cathode wires via the Teflon coated wire 66.

The interengaged frusto-conical tapered surfaces 54 and 28 of the cathode sub-assembly and anode-body sub-assembly and the surfaces 38 and 36 of the anode 24 and housing 22 are precision-machined and are fitted together with an epoxy material of high electrical resistivity and housing 22 are precision-machined and are fitted together with an epoxy material of high electrical resistivity and strength provided therebetween as an adhesive. Because of the precision-machining of these tapered surfaces, and their consequential tight interengagement, this epoxy material is mostly extruded from between the components as the components are joined together, so that only a trace of the epoxy material remains after the assembly of these components. Furthermore, these precision machined surfaces provide the additional advantage of accurate centering of the components of the sensor, which is of assistance in the final shaping of the completed sensor.

In the manufacture of the present sensor, it was determined that method of fabricating a highly effective cathode wire seal was very desirable. Prior art sensors had employed cathodes made either by melting a glass tube around a platinum wire, or by making glass coated wire by melting a glass bead along a length of wire using conventional glass-blowing techniques. These prior art procedures, however, have led to imperfect seals and to a resulting structure which was very fragile and/or difficult to shape.

Furthermore, because of the inconsistencies in the shape of such prior art sensors, particularly when employing the melting of a glass tube around a platinum wire, the incorporation of a prior art cathode into a complete sensor had to depend on the generous use of epoxy adhesive or of other plastic material for joining the cathode to its anode and to the body of the sensor.

In contrast thereto, in the manufacture of the present sensor, and in order to eliminate the above problems of the prior art cathode fabrication and incorporation into a complete sensor, ti was found desirable to allow both machining and shaping of a cathode sub-assembly and to devise a more consistent sealing process.

To that end, the present cathode sub-assembly is made using the housing 51 shown in FIG. 4 and FIG. 6 and in the following referred to generally as the cathode housing, of machinable ceramic Macor ® to which the cathode wires, made of platinum, could be mechanically secured to enable the cathode housing to be placed into an oven where a tube of electrical sealing glass was caused to melt and flow to make the final glass seal 62 shown in FIG. 4.

To minimize stress of the final seal, and even though the ceramic, the sealing glass and the cathode wires have very similar thermal expansion coefficients, it was important to keep the cathode wires in a central, symmetric position. For the same reason of minimizing stress, it was also found desirable to exclude most interior sharp edges which could initiate fracture planes.

Thus the front or left end of the ceramic cathode housing 54 of the cathode sub-assembly has, at the beginning of the manufacture of the cathode sub-assembly, a restricted hole 68 at the end of the tapered internal passage 58 (FIG. 6) so that the cathode wires 60, which in the preferred embodiment comprise platinum and have a diameter of 0.075 mm are held centrally with respect to the internal passage 58. The cathode wires 60 are bent radially outwardly from this hole 68 at the front tip of the cathode housing and are then bent backwardly along the outer surface of the cathode housing 51 as shown in FIG. 6, and held in place by a tightly fitting ceramic cap 70.

The back or right end of the cathode housing 51 is provided at the exterior thereof with a loosely fitting ceramic cap 72, which again holds the cathode wires centrally with respect to the cathode housing because of a small hole 74 therein and which extends along a substantial portion of the cathode housing so as to increase the total weight and stability of the cathode housing 51 and to increase the tension in the cathode wires 60. Ends 61 of the cathode wires 60 are employed to support the housing 51 in a vertical position during the sealing operation.

As can also be seen in FIG. 6, a tube 76 of sealing glass (such as Corning #8940) is provided in the right or back end portion of the internal passage 56 of the cathode housing 51.

During the sealing operation, which is effected by suspending the cathode housing in the above-described manner in a furnace maintained at a temperature of approximately 950° C. for a period of three hours, the glass is caused to melt and to flow downwardly to the front or lowermost end of the internal passage 58 of the cathode housing, where this glass, in solidified form, forms the glass seal 62 (shown in FIG. 4) in sealing contact with the surface of the internal passage 58 of the cathode housing 51 and the cathode wires 60. The restricted opening 68 of the cathode housing and the tight fitting ceramic cap 70, coupled with the relatively high viscosity of the molten glass, do not allow substantial leakage of the molten glass out of the tip of the cathode housing during the sealing operation. The glass seal 62 is annealed by reheating to 423° C. and recooling before any further operations are performed.

The end front portion of the cathode housing, including the cap 70 and the restricted terminal opening 68, is then removed with a diamond saw and ground to provide the front or left tip of the cathode sub-assembly as shown in FIG. 4.

Before use of the sensor, the anode 24 is carefully cleaned, with a soft camel-hair brush and a fine, polishing grade of alumina, using a weak ammonium hydroxide/detergent solution followed by thorough rinsing and a final cleaning with ethanol. The composition of the electrolyte used is empirically determined, and typically contains 0.8% KCl (or 0.75% NaCl+0.03% KCl), 20 mM TAPS buffer @ pH 8.5, with 1 mM DTPA (diethylenetriaminepentaacetic acid, a chelating agent) and 0.1% NP-40 (a non-ionic detergent) as a wetting agent. The actual electrolyte composition has not been found to be very critical and is chosen to be similar t that of solutions in which the sensor 10 is normally used. To improve both long and short term stability of the sensor 10 (thought to arise from a more consistent reference potential of the Ag/AgCl anode) the sensor 10 is connected to its appropriate polarizing voltage (typically 550 mV, anode positive with respect to cathode) and operated in fresh electrolyte without its membrane (described below) for about 1 hour. The sensor current under these conditions is about ten times that with the membrane in place.

Figure 7A:
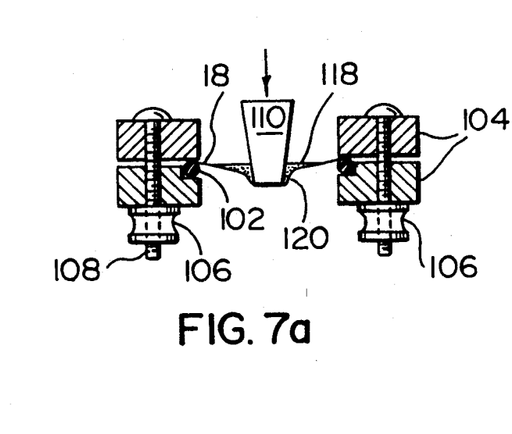
FIGS. 7a, 7b and 7c diagrammatically illustrate successive steps in the application of a membrane to the sensor of FIG. 2.

In order to fit the membrane 18 to the sensor, the membrane 18 is firstly secured a shown in FIG. 7a. More particularly, the membrane is clamped against an O-ring 102 by means of a pair of annular clamps 104, which are tightened together by means of knurled nuts 106 on bolts 108 extending through the annular clamps, in order to clamp the O-ring 102 and the membrane 18 between the inner marginal edge portions of the clamps 104. It will be observed from FIG. 7a that the O-ring 102 is located beneath the membrane 18. The membrane 18 is then pressed downwardly at its center by a pressure member 110, which may conveniently take the form of a #00 silicone rubber stopper or the like, the membrane being cleaned with alcohol before thus being stretched and some of the alcohol being left on the membrane, as indicated by reference numeral 118, to act as a lubricant during such stretching. The stretched portion 120 of the membrane 18 is then applied over the sensor tip as described below.

Figure 7B:
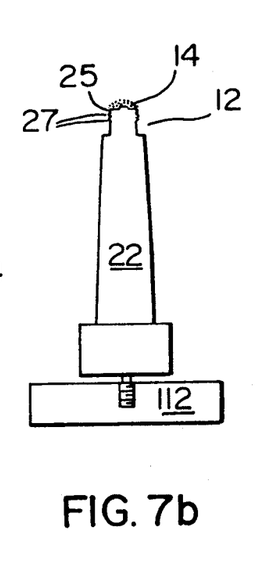

The anode of the sensor 10 being cleaned and preconditioned as described above, the thread of the connector (shown in FIG. 5) is gently screwed into a weighted base 112 (FIG. 7b). A very small amount of silicone grease 12 is then applied around the side of the anode 25 and filling the peripheral serrations 25, 27, and electrolyte 14 is added to the tip of the anode, as shown in FIG. 7b.

Figure 7C:
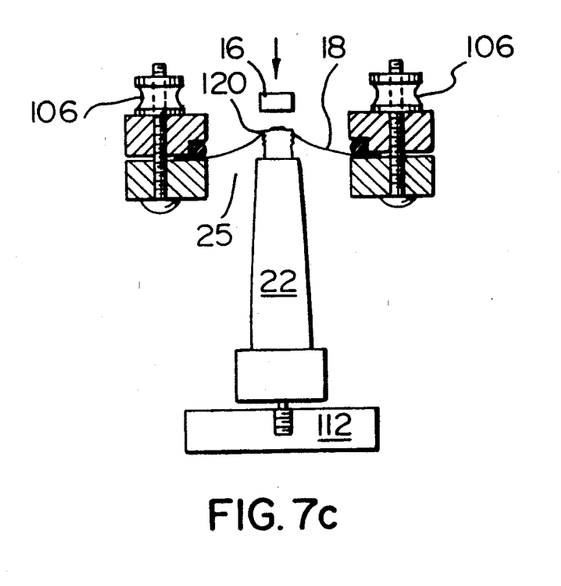

The clamped membrane 18 is then wiped dry of any alcohol and inverted, as shown in FIG. 7c, with the prestretched portion of the membrane 120 stretched over the tip of the sensor 10 in such a manner that the membrane 18 adheres tightly against the first two to three millimeters of the length of the anode (i.e. past the frontmost serration 25 in the anode's periphery).

While maintaining a downward pressure on the clamped membrane, a tight-fitting retaining sleeve 16, made from a cylindrical sleeve of Teflon about 6 mm long and with a 0.75 mm thick wall, is then pushed over the anode so that its leading edge is just past the first serration 25 of the anode. This serration causes the sleeve 16 to be mechanically stable at this position even though the stretching of the retaining sleeve and the further stretching of the membrane caused by the pushing on of the retaining sleeve 16 generates a tensile force which would otherwise tend to push the sleeve 16 back off.

The mechanical stability of the retaining sleeve position at the first serration 25 of the anode allows the membrane to be released from the clamps and substantially trimmed. The nuts 106 of the membrane retaining clamps are loosened, allowing the release of the membrane 18 which is then trimmed close to the retaining sleeve 16 using fine iris scissors. The retaining sleeve 16 is then pushed further over the anode and its second and third serrations 27 to cover completely both the anode and the trimmed peripheral edge of the membrane. This two-step procedure allows no residual membrane edge portion to remain externally to the retaining sleeve 16 and the modest flexibility of said retaining sleeve allows it to follow tightly the contours of the anode periphery thus retaining virtually no trapped gas space. This solves a difficult problem with the use of oxygen sensors in critical applications where any residual membrane external to its retainer would trap gas bubbles or contaminants. As described above, this problem almost always exists with prior art commercial sensors, regardless of the method of containment of the membrane.

The combined effect of the silicone grease, the serrations, the long membrane retaining sleeve and the relatively thick membrane (0.05 mm Teflon film with no surface flaws) lead to an extraordinarily effective seal of the electrolyte.

Operation

The completed sensor was connected to a sensitive current-measuring instrument at a polarizing voltage of 0.55 volts. It was sealed into an air-tight aluminum vacuum chamber (C. J. Koch, the Effect of Oxygen on the Repair of Radiation Damage to Cells and Tissues. In "Advance in Radiation Biology" (Eds J. Lett & H. Adler) Academic Press, New York, 8, pp 273–315, 1976) by way of an Ultra-Torr ® fitting (Cajon). The sensitivity in air at one atmosphere of pressure was established as approximately $5 \times 10^{-9}$ amps (nA) at room temperature. Since air contains about 20.9% oxygen, and 1 atmosphere represents 101.3 kilopascals (kPa) this translates to about 0.25 nA/kPa of oxygen partial pressure.

When the sensor was switched from air (oxygen content 210,000 parts per million [ppm]) into a nitrogen atmosphere (oxygen content as analyzed by Union Carbide, less than 5 ppm) the current dropped exponentially with an initial response-time of 20 seconds to an absolute value corresponding to a value less than 100 ppm over the next 45 minutes. The stability of the zero current was equivalent to less than 20 ppm/day and the noise was of the order of 2 ppm.

The stability of the reading in continuous exposure to air at constant temperature was better than −2% per day after an initial operating time of 1 hour. In sealed containers with solutions held at constant temperature, the response of the sensor was constant within measurement limits (±0.2%). This excellent stability is attributable to the sealing technique of the membrane. A measure of this seal was that the aerobic response of the sensor was not affected by prior continuous exposure to a high vacuum, (less than 0.015 kPa) for 2 weeks.

The above-described test of stability after exposure to high vacuum and some of the following experiments were performed by inserting the sensor, using an Ultra- Torr® fitting (Cajon) into a leak-proof chamber connected via a manifold to a vacuum pump, nitrogen tank, and precision pressure gauge (C. J. Koch, The Effect of Oxygen on the Repair of Radiation Damage to Cells and Tissues. In "Advances in Radiation Biology" (Eds J. Lett & H. Adler) Academic Press, New York, 8, pp 273-315,, 1976).

Another experiment was used to determine whether the sensor could operate independently of hydrostatic pressure. The response of the sensor, initially in air, was monitored after evacuation the chamber to quite a high vacuum (approximately 1 kPa), waiting for sensor equilibrium, and then refilling the chamber with pure nitrogen. The equilibrium response was the same in the partial vacuum as it was following the readmission of pure nitrogen. As mentioned earlier, this is what would be expected if the sensor's response was only sensitive to oxygen partial pressure and was independent of actual hydrostatic pressure.

The linearity of the sensor was tested by filling the chamber with 30% oxygen and then every 5 minutes subjecting to a "gas change". Each gas change was made by evacuating the chamber to 31.9 kPa pressure (as measured by the precision pressure gauge), then refilling the chamber to 101 kPa with pure nitrogen. As long as the vacuum gauge reading was reproducible, the oxygen partial pressure should decrease by the same proportion (roughly 0.32) with each gas change, and therefore a plot of log sensor current vs. number of gas changes should be a straight line (C. J. Koch, Measurement of Very Low Oxygen Tensions in Liquids: Does the Extrapolation Number for Mammalian Survival Curves Decrease After X-irradiation Under Hypoxic Conditions. In: Proc. 6th LH Gray Conference (1974) Institute of Physics, London, England, pp 167-173, 1975). The response of the sensor was not different than the predicted exponential relationship over four decades of oxygen partial pressure if the absolute zero current (approximately 50 ppm in this experiment) was subtracted from all of the readings.

The dependence on stirring speed of the sensor's response in a gas-equilibrated liquid was low. The sensor was placed above a stirred liquid, using a small vial fitted with an Ultra-Torr® fitting (Cajon). The sensor could be lowered into the liquid without causing any change in the gas phase oxygen value because of the O-ring seal of the fitting. The response was essentially unchanged in a slowly stirred, gas-equilibrated liquid and, as would be expected, this response was not dependent on the absolute oxygen level. For a completely unstirred liquid, the response decreased by less than 2% at room temperature.

The temperature response of the sensor in dry gas was about 2.9% per degree C. To measure this, the sensor was simply allowed to equilibrate at various temperatures in a refrigerated air-flow incubator with the temperature measured by a precision mercury thermometer. The Arhenious plot of the data showed an extremely linear relationship with an activation energy of 5 kilocalories per mole (i.e. the sensor response doubled with a temperature increase of approximately 25° C.).

A major problem exists with many prior art sensors due to interference from chemicals other than oxygen. Some such chemicals, like $CO_2$, can affect the pH of the electrolyte and others can (also) participate in the redox reactions of the sensor itself (oxidizing or reducing gases). Still other chemicals, if they can diffuse through or around the membrane barrier, can make the sensor response completely unpredictable. A common example is to have reducing agents present and to be monitoring the oxygen consumption of the auto-oxidation reactions. An equally common result is to observe anomalous currents (i.e. with respect to the oxygen derived current) and/or gross changes in the appearance of the silver anode (due to silver-sulfide for example). The response of the sensors in the present embodiment does not change with $CO_2$, is only minimally sensitive to $N_2O$ (commonly used in radiation chemistry and in medicine) and is not influenced by reducing agents in monitored solutions.

Thus the present sensor exhibits unprecedented accuracy and utility. Many problems associated with the Clark-type sensor have been eliminated or greatly reduced and it now appears feasible to make additional improvements and to test various aspects of the design in an analytical manner. The operation specifications of the sensor offer a particular improvement in the measurement of extremely low oxygen partial pressures or in any situation requiring an extremely stable response. These improvements should allow detailed study of the many processes which are very sensitive to small absolute values of, or changes in, oxygen concentration. In addition, the excellent seal of the relatively thick (0.05 mm) Teflon membrane, allowing exposure of only ceramic and Teflon to a measured solution, allows the sensor to operate in many hostile environments. Thus, the sensor will operate at pH extremes and in many organic and inorganic solvents, thus suggesting many new applications for the measurement of oxygen partial pressures. The operating specifications for the above-described embodiment of the present invention and several commercial sensors are summarized in Table 1.

The sealing methodologies described above for the cathode wires 60 are quite versatile. The number of cathode elements can be changed (from one to four wires have been sealed with success). The size of the cathode wires can be varied to suite a particular requirement (0.025-0.25 mm diameter Pt has been used by the present inventor with an optimal diameter appearing to be 0.075 mm for the membrane used).

It has often been stated, without clearcut experimental evidence, that cathodes other than platinum (e.g. gold) could have electrochemical advantages in polarographic sensors. The described method of melting glass into a heat resistant, machinable container has been used to seal cathode wires such as gold into the ceramic cathode housing even though there is a tremendous mismatch of thermal expansion coefficients. Similarly, it is possible to obtain annular cathodes and anodes by using different types of thick film precious-metal/glass fired composites. It should be possible to include electrically separate elements of combinations of the above to provide sensors with internal references, temperature sensing etc. Until now this type of versatility has only been possible with semiconductor technologies (This Film Electrochemical Electrode and Cell. U.S. Pat. No. 4,062,750, issued Dec. 13, 1977 to J. F Butler).

However these more sophisticated approaches have not yet been attempted because the specifications of the present devices already represent a many fold improvement over commercially available devices.

Similarly, the use of inert yet machinable ceramic throughout allows for the custom shaping of the completed sensor and its adaptation to all sorts of unusual physical situations. The chemical inertness of all exposed surfaces (ceramic and Teflon) has been found to be particularly advantageous in oxygen measurements using tissue culture and ultrapure chemical environments. The assembled sensors can be sterilized and/or cleaned by short or long-term exposure to pH extremes or solvents without effects on subsequent operation (the present inventor typically uses 70% ethanol at pH 2). The sensors have been used to measure oxygen consumption in heavily irradiated solutions and some have been exposed to several megarads of ionizing radiation without any degradation in response—these doses can cause the embrittlement of many plastics.

The enhanced sensitivity and stability of the present sensors will allow the detailed analysis of oxygen dependent reactions which are beyond the reach of current technology. It is also possible to consider improvements in the many other uses for polarographic devices. Even non-polarographic uses for such devices are possible. For example, the present sensors can be used to measure air pressure with a linear range of four orders of magnitude.

TABLE 1

CHARACTERISTICS OF FOUR OXYGEN SENSORS

| Parameter | Sensor Number[1] | | | |
| --- | --- | --- | --- | --- |
| | #1 | #2 | #3 | #4 |
| Sensitivity[2] (nA/kPa) | 0.07 | 16.0 | 0.5 | 0.25 |
| Linearity (decades-measured) | 2 | 2 | — | 4 |
| Stability (±%/hr) | 0.5% | NS | NS | 0.1 |
| Min. Zero Current (nA) | <0.1 | <3 | NS | <0.003 |
| Temperature Coef. (%/°C.) | 4 | 4 | 5 | 2.9 |
| Response Time[3] (Sec/decades of response) | 2/2 | 3/2 | 4/1.5 | 20/4 |
| Polarizing Voltage (V) | 0.75 | 0.8 | 0.7 | 0.55 |
| Membrane Thickness (mm) | 0.025 | 0.013 | 0.025 | 0.05 |
| Membrane Material[4] | PP | T,PP | PE | T |
| Membrane Retainer[5] | O | O | O | TC |
| Body Material[6] | A | E | G/SF | C |
| Electrolyte[7] | 3K/D | KS | 0.9N | 0.9B/Ch/D |
| Storage | Dry | Dry | Dry | Wet/Dry |

Notes
[1] #1 is Beckman 325814, #2 is Yellow Springs 5331, #3 is Diamond Electrotech 730, #4 is present design.
[2] Abbreviations: 1 nA(nanoamp) = $10^{-9}$ amps, 1 kPa(kilopascal) 0.01 atmospheres. NS means not specified.
[3] Range unspecified. Values quoted are measured using membranes supplied by manufacturer.
[4] PP is polypropylene, PE is polyethylene, T is Teflon.
[5] O is O-ring, TC is Teflon cylinder.
[6] A is acrylic, E is epoxy, G/SF is glass/silver foil, C is ceramic.
[7] 3K is 3% KCl, D is detergent, KS is saturated KCl, 0.9N is 0.9% NaCl, 0.9B is 0.9% NaCl buffer and Ch is chelator.

I claim:

1. A method for making a polarographic oxygen sensor, comprising the steps of:
   a) providing an elongate cathode housing formed of an inert, electrically non-conducting machinable ceramic material and having a longitudinal passage therein extending into an opening of lesser diameter than the passage at a tip end of the housing;
   b) securing an elongate cathode comprising at least one cathode wire through said longitudinal passage, symmetrically spaced from walls of said passage;
   c) providing molten glass in said passage in which the cathode is secured;
   d) allowing the molten glass to flow into said opening, toward said secured cathode, and toward said walls; and
   e) subsequently allowing said molten glass to solidify and form a glass seal in said passage between the cathode and the cathode housing along a substantial length of the cathode.

2. A method as claimed in claim 1, further comprising the steps of disposing said cathode housing with glass seal in an axial passage of an outer, sensor housing with the tip end of said cathode housing protruding therefrom; mounting an anode at the tip end of said cathode housing; stretching a flexible membrane externally over the tip end of said cathode housing and anode; providing a cylindrical retainer over a portion of the membrane covered tip end; removing a marginal edge portion of said membrane adjacent to said retainer; and displacing said retainer over said sensor housing so as to entirely cover a remaining peripheral edge of the membrane between said retainer and an exterior surface of said sensor housing.

3. A method as claimed in claim 2, wherein said retainer is retained on said tip end during the removal of said marginal edge of said membrane by at least one circumferential serration on a surface of said anode.

4. A method as claimed in claim 1, additionally comprising disposing said cathode housing with glass seal in an axial passage of an outer, sensor housing with the top end of said cathode housing protruding therefrom, mounting an anode at the tip end of said cathode housing, and machining an exterior surface of the sensor housing for sealing into a leakproof fitting.

5. A method as claimed in claim 1, wherein said step of providing molten glass comprises disposing a glass tube within said passage between said cathode and walls, and heating the secured cathode, cathode housing and glass tube between the cathode and walls sufficiently to cause said glass tube to become molten.

* * * * *